United States Patent [19]

Marquis et al.

[11] Patent Number: 5,093,506

[45] Date of Patent: Mar. 3, 1992

US005093506A

[54] REMOVAL OF ACIDIC CONTAMINANTS FROM TERTIARY BUTYL HYDROPEROXIDE

[75] Inventors: Edward T. Marquis, Austin; John R. Sanderson, Leander; Robert A. Meyer, Austin, all of Tex.

[73] Assignee: Texaco Chemical Company, White Plains, N.Y.

[21] Appl. No.: 400,901

[22] Filed: Aug. 30, 1989

[51] Int. Cl.[5] .......................................... C07D 301/32
[52] U.S. Cl. .................................. 549/529; 549/541; 568/571; 568/909.8; 568/910
[58] Field of Search ................ 549/529, 541; 568/571, 568/909.8, 910

[56] References Cited

U.S. PATENT DOCUMENTS

| | | | |
|---|---|---|---|
| 3,475,498 | 10/1969 | Choo | 549/529 |
| 3,819,663 | 6/1974 | Levine et al. | 549/529 |
| 3,947,500 | 3/1976 | Kollar | 549/529 |

*Primary Examiner*—Alan L. Rotman
*Assistant Examiner*—Ba K. Trinh
*Attorney, Agent, or Firm*—Jack H. Park; Kenneth R. Priem; Carl G. Ries

[57] ABSTRACT

The distillation product fraction obtained from an isobutane oxidation reaction product after the removal of unreacted isobutane will contain tertiary butyl hydroperoxide, tertiary butyl alcohol and carboxylic acid contaminants such as formic acid, acetic acid and isobutyric acid. It has been discovered that when the distillation product fraction is treated with about ½ to 1 equivalents of calcium oxide and/or calcium hydroxide based on the carboxylic acid content of the distillate product fraction, a portion of the carboxylic acid contaminants will precipitate thus partially purifying the distillation product fraction so that, thereafter, molybdenum precipitation will be substantially inhibited when the thustreated distillation product fraction is used as a feedstock for an epoxidation reaction wherein tertiary butyl hydroperoxide is reacted with an olefin in the presence of a soluble molybdenum catalyst to provide an olefin epoxide and additional tertiary butyl hydroperoxide.

14 Claims, 1 Drawing Sheet

REMOVAL OF ACIDIC CONTAMINANTS FROM TERTIARY BUTYL HYDROPEROXIDE

BACKGROUND OF THE INVENTION

1. Field of the Invention

This invention relates to a method for the treatment of a solution of tertiary butyl hydroperoxide in tertiary butyl alcohol to be used as a feedstock in a molybdenum catalyzed olefin epoxidation process in order to inhibit precipitation of the molybdenum catalyst during the epoxidation reaction. More particularly, this invention relates to a method for the partial removal of acidic impurities such as formic acid, acetic acid, isobutyric acid, etc., from a solution of tertiary butyl hydroperoxide in tertiary butyl alcohol to be used as a feedstock in an olefin epoxidation process, such as a process wherein propylene is catalytically reacted with tertiary butyl hydroperoxide in solution in tertiary butyl alcohol in the presence of a catalytic amount of a soluble molybdenum compound in order to inhibit precipitation of the molybdenum catalyst during the epoxidation reaction.

More particularly, this invention relates to a method for the pretreatment with calcium hydroxide and/or calcium oxide of a distillation fraction to be used as a feedstock in a molybdenum catalyzed olefin epoxidation process wherein tertiary butyl hydroperoxide is reacted with an olefin, such as propylene, in solution in tertiary butyl alcohol in an epoxidation reaction zone in order to provide propylene oxide and additional tertiary butyl alcohol, the distillation fraction comprising a solution of tertiary butyl hydroperoxide in tertiary butyl alcohol contaminated with acidic impurities such as formic acid, acetic acid, isobutyric acid, etc., the improvement of the present invention comprising the pretreatment of the distillation fraction with an amount of calcium oxide and/or calcium hydroxide sufficient to partially precipitate the acidic impurities and the removal of the precipitate, whereby, when the thus-treated distillation fraction is used as a feed stock in the epoxidation reaction process, the precipitation of the molybdenum catalyst during the epoxidation reaction is substantially inhibited.

2. Background of the Present Invention

When an olefin epoxide, such as propylene oxide, is to be prepared from the corresponding olefin, such as propylene, by reacting the olefin in organic solvent solution with tertiary butyl hydroperoxide in the presence of a soluble molybdenum catalyst, it is conventional practice to prepare the hydroperoxide feedstock by the non-catalytic or catalytic oxidation of isobutane with oxygen in an oxidation reaction zone to provide an oxidation reaction product comprising unreacted isobutane, tertiary butyl hydroperoxide, tertiary butyl alcohol and oxygen-containing impurities.

It is also conventional practice to remove the unreacted isobutane from the initial oxidation reaction product by distillation and to use the remaining distillation product fraction (normally a bottoms fraction) as the feedstock for the molybdenum-catalyzed reaction of an olefin with the tertiary butyl hydroperoxide. This is advantageous because the tertiary butyl alcohol present in the initial oxidation reaction product serves as a solvent for the peroxidation reaction and because the co-product of the peroxidation reaction is tertiary butyl alcohol, derived from the tertiary butyl hydroperoxide reactant. As a consequence, product work-up is simplified because there is no need to use an extraneous solvent. Also, tertiary butyl alcohol is widely used in motor fuels to enhance the octane characteristics of the motor fuels.

PRIOR ART

It is known to react propylene with tertiary butyl hydroperoxide in the presence of a soluble molybdenum catalyst to provide a reaction product comprising propylene oxide and tertiary butyl alcohol. See, for example, Kollar U.S. Pat. No. 3,350,422, Kollar U.S. Pat. No. 3,351,635, and Russell U.S. Pat. No. 3,418,340.

It is also known to prepare soluble molybdenum catalysts to catalyze the reaction as disclosed, for example, in Bonetti et al. U.S. Pat. No. 3,480,563, Shum et al. U.S. Pat. No. 4,607,113, Marquis et al. U.S. Pat. No. 4,626,596, Marquis et al. U.S. Pat. No. 4,650,886, Marquis et al. U.S. Pat. No. 4,703,027, etc.

It has also been recognized in the prior art that it is desirable to conduct the molybdenum-catalyzed reaction between the propylene and tertiary butyl hydroperoxide in a reaction medium of reduced acidity. Thus, Kollar U.S. Pat. No. 3,350,422 states that it is advantageous to use basic substances such as alkali metal compounds or alkaline earth metal compounds with the catalyst in order to reduce acidity. Similar disclosures are found in Kollar U.S. Pat. No. 3,351,635 and Russell U.S. Pat. No. 3,418,340.

Wu et al. U.S. Pat. No. 4,217,287 discloses a process wherein the reaction is conducted in the presence of barium oxide in order to "stabilize the catalyst". Becker U.S. Pat. No. 4,262,143 discloses a related process for preparing ethyl benzene hydroperoxide. The ethyl benzene hydroperoxide is prepared by the oxidation of ethyl benzene with molecular oxygen in the presence of a small amount of a hydroxide or salt of sodium or potassium. In another process, Iwaki et al. U.S. Pat. No. 4,293,720 discloses a liquid phase process for the preparation of aromatic peroxides by the liquid phase oxidation of an aromatic compound containing a secondary alkyl group with molecular oxygen in the presence of a basic aqueous solution of a copper compound catalyst which also contains cupric carbonate and an alkali metal carbonate and/or an alkali metal bicarbonate.

Kollar U.S. Pat. No. 3,860,662 is directed to an improvement in his basic process relating to the recovery of alcohols from the reaction product, which product is stated to be of an acidic nature, wherein a basic material such as an alkali metal or alkaline earth metal compound is added to the reaction mixture. Kollar U.S. Pat. No. 3,947,500 discloses a method for treating the reaction product formed by the reaction of an organic hydroperoxide with an olefin wherein an organic alcohol is formed as a by-product. It is stated that the alcohol tends to dehydrate and that to at least partially overcome this problem the oxidation reaction product is treated with an alkali metal or an alkaline earth metal compound. Kollar states that the alkali metal or alkaline earth metal compound can be added to the epoxidation reactor or to the reaction product.

Sorgenti U.S. Pat. No. 3,573,226 discloses a method wherein a molybdenum-containing catalyst solution is prepared by incorporating metallic molybdenum into the distillate bottoms fraction of an epoxidation reaction product followed by heating of the resultant mixture in order to form a soluble molybdenum-containing reaction product which can be used to catalyze the epoxidation reaction.

The molybdenum-catalyzed epoxidation of alpha olefins and alpha substituted olefins with hydroperoxides less stable than tertiary butyl hydroperoxide may be accomplished according to U.S. Pat. 3,862,961 to Sheng, et al. by employing a critical amount of a stabilizing agent consisting of a $C_3$ to $C_9$ secondary or tertiary monohydric alcohol, such as tertiary butyl alcohol. Citric acid is used to minimize the iron-catalyzed decomposition of the organic hydroperoxide without adversely affecting the reaction between the hydroperoxide and the olefin in a similar oxirane producing process taught by Herzog in U.S. Pat. 3,928,393. The inventors in U.S. Pat. 4,217,287 discovered that if barium oxide is present in the reaction mixture, the catalytic epoxidation of olefins with organic hydroperoxides can be successfully carried out with good selectivity to the epoxide based on hydroperoxide converted when a relatively low olefin to hydroperoxide mole ratio is used. The alphaolefinically unsaturated compound should be added incrementally to the organic hydroperoxide.

Selective epoxidation of olefins with cumene hydroperoxide (CHP) can be accomplished at high CHP to olefin ratios if barium oxide is present with the molybdenum catalyst as reported by Wu and Swift in "Selective Olefin Epoxidation at High Hydroperoxide to Olefin Ratios," *Journal of Catalysis*, Vol. 43, 380–383 (1976).

Maurin U.S. Pat. No. 3,931,076 is directed to a method for recovering molybdenum catalyst values from a peroxidation reaction product for recycle. Maurin discloses one of three techniques. In accordance with the first embodiment, the residue fraction is calcined to provide molybdenum trioxide which is then used to prepare a soluble molybdenum compound by reaction with aqueous ammonia. In a second embodiment, the molybdenum-containing fraction is treated with aqueous ammonia without calcining to form an ammonium molybdate which is treated with a polyalcohol to give a molybdic ester. In a third embodiment, the molybdenum-containing fraction is treated with gaseous ammonia in order to form an ammonium molybdate precipitate which can be recovered by filtration.

As can be seen by the foregoing, when it is desired to reutilize the molybdenum catalyst initially used to catalyze the epoxidation reaction between an olefin such as propylene and a hydroperoxide such as tertiary butyl hydroperoxide, the used molybdenum catalyst is normally concentrated in a distillation bottoms fraction which contains other impurities such that direct recycle, without treatment, is normally impractical.

Harvey U.S. Pat. No. 3,449,217 is directed to a process for the recovery of tertiary butyl hydroperoxide from a mixture comprising tertiary butyl hydroperoxide, tertiary butyl alcohol and organic acids and esters resulting from the liquid phase oxidation of isobutane by a process which minimizes hydroperoxide decomposition. This is done by accomplishing the distillation while the product has an effective pH of below about 9. The patentee teaches the treatment of the reactor effluent with a neutralizing agent such as an alkali metal or an alkaline earth metal hydroxide.

SUMMARY OF THE INVENTION

It has been discovered in accordance with the present invention that when a solution of tertiary butyl hydroperoxide in tertiary butyl alcohol is treated with a conventional base, such as sodium hydroxide, sodium carbonate, sodium butoxide, potassium hydroxide, potassium butoxide, ammounium hydroxide, etc., precipitation of the soluble molybdenum catalyst used to catalyze the reaction of an olefin with tertiary butyl hydroperoxide in solution in tertiary butyl alcohol can unpredictably occur when the propylene and the soluble molybdenum catalyst are added to a base-treated solution of tertiary butyl hydroperoxide in tertiary butyl alcohol.

It has been further discovered, in accordance with the present invention, that the precipitation of the soluble molybdenum catalyst from the solution of olefin and tertiary butyl hydroperoxide in solution in tertiary butyl alcohol in the epoxidation reaction zone can be substantially inhibited when a distillation fraction comprising a solution of tertiary butyl hydroperoxide in tertiary butyl alcohol which is contaminated with acidic impurities such as formic acid, acetic acid, isobutyric acid, etc., is treated with calcium oxide and/or calcium hydroxide for the partial removal of such acidic impurities before the the solution of olefin and tertiary butyl hydroperoxide in solution in tertiary butyl alcohol is charged to the epoxidation reaction zone.

One aspect of the present invention is the treatment with calcium oxide and/or calcium hydroxide of a distillation fraction comprising a solution of tertiary butyl hydroperoxide in tertiary butyl alcohol contaminated with carboxylic acid impurities in order to enhance the utility of the distillation fraction as a feed component for an epoxidation reaction.

Another aspect of the present invention is a process wherein isobutane is charged to an oxidation reaction zone where it is reacted under oxidation reaction conditions with an amount of oxygen sufficient to provide an oxidation reaction mixture comprising about 50 to 80 wt.% of unreacted isobutane, together with tertiary butyl hydroperoxide, tertiary butyl alcohol and impurities, including about 1 wt.% or more of carboxylic acid impurities such as formic acid, acetic acid and isobutyric acid, wherein the oxidation reaction mixture is separated by distillation into a distillate recycle isobutane fraction and a heavier distillation fraction comprising the tertiary butyl hydroperoxide, the tertiary butyl alcohol and and the carboxylic acid impurities, wherein the heavier distillation fraction is treated with about ½ to 1 equivalents, based on the carboxylic acids, of calcium oxide and/or calcium hydroxide to form a treated fraction containing a precipitate and wherein the precipitate is separated from the treated fraction to provide a feed fraction comprising the tertiary butyl hydroperoxide, the tertiary butyl alcohol and a lesser quantity of the carboxylic acid impurities.

Another aspect of the present invention is the epoxidation of an olefin with tertiary butyl hydroperoxide in an epoxidation reaction zone under epoxidation reaction conditions in the presence of a catalytic amount of a soluble molybdenum catalyst compound wherein the olefin and the soluble molybdenum catalyst are added to a solution of tertiary butyl hydroperoxide in tertiary butyl alcohol, the solution of tertiary butyl hydroperoxide in tertiary butyl alcohol being a distillation fraction comprising a solution of tertiary butyl hydroperoxide in tertiary butyl alcohol containing about 1 to about 5 wt.% of $C_1$ to $C_4$ carboxylic acid impurities that has been treated with calcium oxide and/or calcium hydroxide for the partial removal of carboxylic acid impurities therefrom before the olefin and the soluble molybdenum catalyst are added thereto.

Yet another aspect of the present invention is a process wherein an olefin is reacted with tertiary butyl hydroperoxide in an epoxidation reaction zone in solution in tertiary butyl alcohol under epoxidation reaction conditions in the presence of a catalytic amount of a soluble molybdenum catalyst compound to provide an epoxidation reaction mixture comprising unreacted propylene, propylene oxide, additional tertiary butyl alcohol, tertiary butyl hydroxide, and carboxylic acid impurities such as formic acid, acetic acid, isobutyric acid, etc., wherein the epoxidation reaction mixture is separated by distillation into a distillate recycle propylene fraction, a distillate propylene oxide product fraction, a distillate tertiary butyl alcohol product fraction containing about 1 to about 5 wt.% of $C_1$ to $C_4$ carboxylic acid impurities and a heavier distillation fraction comprising tertiary butyl alcohol, tertiary butyl hydroperoxide and impurities including the molybdenum catalyst, wherein the distillate tertiary butyl alcohol fraction is treated with about ½ to 1 equivalents of calcium oxide and/or calcium hydroxide, based on the carboxylic acid content of the distillate fraction for the partial precipitation of the carboxylic acid impurities therefrom, and wherein the thus-treated distillate fraction, after the removal of the precipiate therefrom, is recycled to the epoxidation reaction zone.

A preferred embodiment of the present invention is a process:

a. wherein isobutane is reacted with oxygen in an oxygenation reaction zone to form a reaction product comprising unreacted isobutane, tertiary butyl alcohol, tertiary butyl hydroperoxide and oxygen-containing impurities including di-tertiary butyl peroxide, acetone, methanol, and carboxylic acid impurities including acetic acid, formic acid, and isobutyric acid, b. wherein the reaction product is charged to a distillation zone where it is separated into a lighter isobutane recycle distillate fraction and a heavier distillation fraction comprising a solution of at least a 30 wt.% tertiary butyl hydroperoxide in tertiary butyl alcohol which is contaminated with tertiary butyl peroxide, acetone, methanol, and carboxylic acid impurities such as formic acid, acetic acid, isobutyric acid, etc., c. wherein said heavier distillation fraction is charged to a first treatment zone where it is reacted with about ½ to about 1 equivalents of calcium oxide and/or calcium hydroxide, based on the carboxylic acid content of the heavier distillation fraction to form a slurry of partially precipitated carboxylic acid impurities, d. wherein said slurry is charged to a separation zone and resolved therein into a solids fraction and a filtrate fraction comprising a tertiary butyl alcohol solution of tertiary butyl hydroperoxide, e. wherein said filtrate fraction comprising said tertiary butyl alcohol solution of tertiary butyl hydroperoxide is charged to an epoxidation zone together with a soluble molybdenum catalyst and propylene, f. wherein epoxidation reaction conditions are established in said epoxidation reaction zone for the molybdenum catalyzed reaction of the propylene with the tertiary butyl hydroperoxide contained in said filtrate fraction to form an epoxidation reaction product containing propylene oxide and additional tertiary butyl alcohol, and g. wherein propylene oxide and tertiary butyl alcohol are recovered from the said epoxidation reaction product.

A specific embodiment of the present invention is a process:

a. wherein isobutane is reacted with oxygen in an oxygenation reaction zone to form an oxidation reaction product comprising unreacted isobutane, tertiary butyl alcohol, tertiary butyl hydroperoxide and oxygen-containing impurities such as di-tertiary butyl peroxide, acetone, methanol, and carboxylic acid impurities including acetic acid, formic acid and isobutyric acid, b. wherein the reaction product is charged to a first distillation zone where it is separated into a lighter isobutane recycle distillate fraction and a first heavier distillation fraction comprising at least a 30 wt.% solution of tertiary butyl hydroperoxide in tertiary butyl alcohol which is contaminated with tertiary butyl peroxide, acetone, methanol, and about 1 wt.% or more of carboxylic acid impurities such as formic acid, acetic acid, isobutyric acid, etc., c. wherein the first heavier distillation fraction is charged to a first treatment zone where it is reacted with about ½ to 1 equivalents of calcium oxide and/or calcium hydroxide, based on the carboxylic acid content of the first heavier distillation fraction, to form a first slurry of partially precipitated carboxylic acid impurities, d. wherein the first slurry is charged to a first separation zone and resolved therein into a solids fraction and a first filtrate fraction comprising a tertiary butyl alcohol solution of tertiary butyl hydroperoxide containing a reduced quantity of carboxylic acids, e. wherein the first filtrate fraction comprising the tertiary butyl alcohol solution of tertiary butyl hydroperoxide is charged to an epoxidation zone together with a soluble molybdenum catalyst and propylene, f. wherein epoxidation reaction conditions are established in the epoxidation reaction zone for the molybdenum catalyzed reaction of the propylene with the tertiary butyl hydroperoxide contained in the first filtrate fraction to form an epoxidation reaction product containing unreacted propylene, propylene oxide, additional tertiary butyl alcohol, unreacted tertiary butyl hydroperoxide and impurities, including about 1 to about 5 wt.% of $C_1$ to $C_4$ carboxylic acid impurities such as formic acid, acetic acid, isobutyric acid, etc., g. wherein the epoxidation reaction product is charged to a second distillation zone where it is separated into a distillate propylene recycle fraction, a distillate propylene oxide product fraction, a distillate tertiary butyl alcohol product fraction containing impurities including about 1 to about 5 wt.% of $C_1$ to $C_4$ carboxylic acid, tertiary butyl hydroperoxide, etc., and a heavy distillation fraction comprising tertiary butyl alcohol, unreacted tertiary butyl hydroperoxide and impurities, including the molybdenum catalyst, h. wherein the distillate tertiary butyl alcohol product fraction containing impurities including about 1 to about 5 wt.% of $C_1$ to $C_4$ carboxylic acid, tertiary butyl hydroperoxide, etc., is reacted in a treating zone with about ½ to 1 equivalents of calcium oxide and/or clacium hydroxide, based on the carboxylic acid content of the fraction being treated, to form a slurry of partially precipitated carboxylic acid impurities, i. wherein the thus-formed slurry is charged to a separation zone and resolved therein into a solids fraction and a second filtrate fraction containing a reduced quantity of the carboxylic acid impurities.

DETAILED DESCRIPTION OF THE INVENTION

As noted above, a principal aspect of the present invention is the discovery that precipitation of the molybdenum catalyst in the molybdenum catalyzed epoxidation of an olefin with base-treated tertiary butyl hydroperoxide is substantially eliminated when the distillation fraction used as one of the feed components for the epoxidation reaction (a solution of tertiary butyl hydroperoxide in tertiary butyl alcohol contaminated with carboxylic acid impurities) is treated with about ½ about 1 equivalents of calcium oxide and/or calcium hydroxide, based on the carboxylic acids in the distillation fraction to form calcium salts of the carboxylic acids that can be removed by filtration before the distillation fraction is used in the epoxidation reaction. Thus, the calcium oxide and/or calcium hydroxide treating step is one of the several steps involved in converting isobutane and propylene to tertiary butyl alcohol and propylene oxide.

Oxidation of Isobutane

The first step in the integrated process for converting isobutane and propylene to tertiary butyl alcohol and propylene oxide is the oxidation of isobutane with oxygen to provide tertiary butyl hydroperoxide for use as a reactant and tertiary butyl alcohol for use as a solvent.

The oxidation of isobutane with molecular oxygen is conducted in an oxidation reaction zone in liquid phase. It is not necessary to use an oxidation catalyst, although one is sometimes employed. The oxidation is preferably conducted at a moderate pressure because of the volatility of isobutane, such as a pressure of about 50 to 1,000 psig. The oxidation reaction is usually conducted at a temperature of about 40° to about 200° C., such as a temperature of about 80° to about 180° C. and, more preferably, from about 90° to about 150° C.; reaction time and reaction conditions being correlated to provide a desired conversion of the isobutane, such as a conversion of about 10 to about 75% and, more preferably, from about 20 to about 50%. The composition of the oxidation reaction product is given in Table I.

The oxidation reaction product discharged from the oxidation reaction zone will normally have the composition shown in Table I.

TABLE I
COMPOSITION OF INITIAL OXIDATION REACTION PRODUCT

| Component | General Range, Wt. % | Preferred Range, Wt. % |
|---|---|---|
| Isobutane | 25–90 | 50–80 |
| t-butyl hydroperoxide | 70–0 | 25–55 |
| t-butyl alcohol | 0–70 | 25–55 |
| Others* | 0.5–10 | 0.5–5 |

*Includes di-tertiary butyl peroxide, acetone, methanol, acetic acid, formic acid, isobutyric acid and other oxygenated impurities.

The oxidation product is normally withdrawn from the oxidation reaction zone and charged to a first distillation zone where it is normally separated into a lighter unreacted isobutane fraction, which is suitably recycled to the oxidation reaction zone, and a heavier fraction comprising tertiary butyl alcohol, tertiary butyl hydroperoxide and impurities, including carboxylic acid impurities such as formic acid, acetic acid and isobutyric acid.

Calcium Oxide/Calcium Hydroxide Treatment

In accordance with the present invention, the heavy distillation fraction recovered in the first distillation zone after isobutane oxidation is charged to a calcium oxide/calcium hydroxide treating zone where it is treated with calcium oxide and/or calcium hydroxide. It will be understood that the treatment with calcium oxide and/or calcium hydroxide will be effective for partially removing acidic impurities, including carboxylic acid impurities but that other impurities such as acetone, methanol, etc., will not be significantly affected by the treatment.

The heavy distillation fraction can be treated on a batch basis or on a continuous basis under treating conditions including a temperature of about 25° to about 100° C. and a pressure of about 15 to about 500 psig. for a treating time of about 0.25 to about 300 hours in order to react about ½ to 1 equivalents of calcium oxide or calcium hydroxide, based on the carboxylic acid content of the heavy distillation fraction with about an equivalent amount of the carboxylic acid impurities in the heavy distillation fraction (e.g., formic acid, acetic acid, isobutyric acid) to form a slurry of precipitated calcium salts of the carboxylic acids in the heavy distillation fraction.

Figure 1:
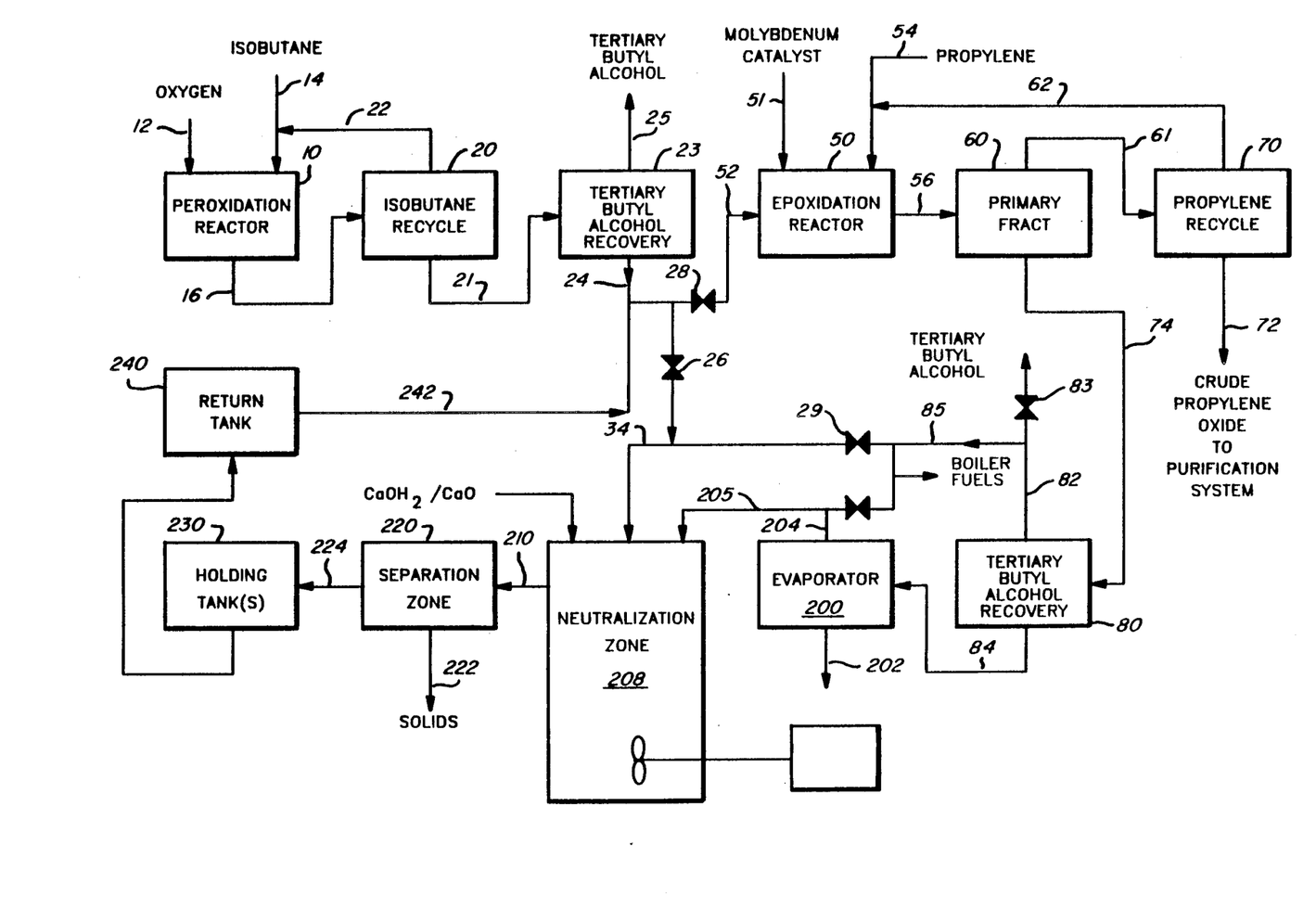
The drawing is a schematic flow sheet with conventional parts omitted showing the general reaction and recovery sequence that is used in the practice of the preferred embodiment of the present invention.

When the calcium oxide/hydroxide treatment is one step in a continuous process, as illustrated in the drawing, the treatment is preferably conducted on a continuous basis in a treating vessel, such as an autoclave, equipped with an agitator and suitable temperature control means, such as a cooling jacket. The autoclave treatment is preferably conducted by continuously charging both the heavy distillation fraction and finely divided calcium oxide and/or calcium hydroxide to the autoclave at a temperature of about 75° to about 100° C., a pressure of about 100 to about 500 psig. for a treating time of about 0.25 to about 5 hours in order to permit a substantial portion of the carboxylic acid impurities in the heavy distillation fraction (e.g., formic acid, acetic acid, isobutyric acid) to react with the calcium oxide and/or calcium hydroxide to form a slurry of the precipitated calcium salts of the carboxylic acids in the heavy distillation fraction. Again, about ½ to about 1 equivalents of calcium oxide or calcium hydroxide should be used, based on the carboxylic acid content of the heavy distillation fraction.

The thus-formed slurry is charged to a separation zone containing any suitable separating means such as a centrifugation means, filtration means, etc., wherein the precipitate and other solids, if any, are separated to provide a solids product and a filtrate comprising the treated, partially purified solution of tertiary butyl hydroperoxide in tertiary butyl alcohol.

Synthesis of Propylene Oxide and Tertiary Butyl Alcohol

The filtrate from the separation zone is charged to an epoxidation zone containing an epoxidation reactor to which an olefin such as an alpha olefin containing 3 to 10 carbon atoms, such as propylene is also charged. A molybdenum catalyst is also charged to the epoxidation reactor, preferably in admixture with the base-treated filtrate comprising the tertiary butyl alcohol solution of tertiary butyl hydro-peroxide. An epoxidation reaction is conducted in the epoxidation reactor under epoxidation reaction conditions in order to convert the olefin to the corresponding olefin epoxide and the tertiary butyl hydroperoxide to tertiary butyl alcohol.

Under ambient conditions t-butyl hydroperoxide is a comparatively stable material. However, as the temperature increases, the hydroperoxide tends to become "destabilized" so that thermal and/or catalytic decomposition will be initiated leading to the formation of unwanted by-products such as ketones, lower molecular weight alcohols, tertiary alcohols, oxygen, etc. This is a particularly troublesome problem at temperatures of 50° to 180° C (e.g., 100° to 130° C.) which are normally used when tertiary butyl hydroperoxide is catalytically reacted with an olefin to form an olefin epoxide. This problem can be at least partially overcome by conducting the epoxidation reaction in the presence of an excess of the olefin reactant. The unreacted olefin must be separated from the epoxide reaction product for recycle.

Epoxidation Reactants and Catalysts a) The Olefin

The method of this invention can be used to epoxidize $C_3$-$C_{10}$ olefinically unsaturated compounds such as substituted and unsubstituted aliphatic and alicyclic olefins. The process is particularly useful in epoxidizing compounds having at least one double bond situated in the alpha position of a chain or internally. Representative compounds include propylene, normal butylene, isobutylene, pentenes, methyl pentenes, hexenes, octenes, dodecenes, cyclohexene, substituted cyclohexenes, butadiene, styrene, substituted styrenes, vinyl toluene, vinyl cyclohexene, phenyl cyclohexenes and the like.

The invention finds its greatest utility in the epoxidation of propylene and propylene is epoxidized particularly advantageously by the inventive process.

The selectivity to olefin epoxide, on the basis of hydroperoxide converted, can be enhanced when the hydroperoxide is charged to the reaction zone in at least a 30 wt.% solution of the corresponding product alcohol and the olefin is charged to the reaction zone in an amount relative to the hydroperoxide charged to the reaction zone such that about 0.9 to 2 moles of olefin are charged per mole of hydroperoxide charged.

b) The Tertiary Butyl Hydroperoxide

The TBHP should be charged in at least a 30 wt.% solution in t-butyl alcohol, and preferably about a 40 to 75 wt.% solution.

c) The Molybdenum Catalyst

Catalysts suitable for the epoxidation method of this invention are molybdenum catalysts that are soluble in the reaction medium.

Examples of suitable soluble catalysts include molybdenum compounds such as molybdenum octoate, molybdenum naphthenate, molybdenum acetyl acetonate, molybdenum/alcohol complexes, molybdenum/glycol complexes, etc.

Other catalysts found to be useful are the molybdenum complexes of alkylene glycols with molybdenum compounds as described in U.S. Pat. No. 4,626,596 issued Dec. 12, 1986 and entitled "Improved Synthesis of Molybdenum/Alkylene Glycol Complexes Useful as Epoxidation Catalysts". Briefly, these complexes are made by reacting an ammonium-containing molybdenum compound with an alkylene glycol in the presence of water at an elevated temperature, such as about 80° to 130° C. The ammonium-containing molybdenum compound is preferably ammonium heptamolybdate tetrahydrate or ammonium dimolybdate hydrate. The alkylene glycols are preferably ethylene glycol and/or propylene glycol although others have been found to be useful.

Still other catalysts found to be useful in the practice of the present invention are molybdenum complexes of monohydric alcohols as described in U.S. Pat. No. 4,650,886 issued Dec. 2, 1986 and entitled "Improved Synthesis of Molybdenum/Alcohol Complexes useful as Epoxidation Catalysts". Briefly, an alkanol such as 2-ethyl hexanol is reacted with a molybdenum oxide in the presence of ammonium hydroxide or by reacting the alkanol with ammonium heptamolybdate in the presence of a controlled amount of water.

d) Epoxidation Reaction Conditions

The epoxidation reaction may be conducted at a temperature in the range of 50°–180° C. with a preferred range of between 90° and 140° C. An especially preferred range is 100 to 130° C. with about 110° C.–120° C. being the most preferred single stage operating temperature.

The catalyst concentrations in the method of this invention should be in the range of 50 to 1,000 ppm (0.01 to 0.10 wt.%) based on the total reactant charge. Catalyst concentration is calculated as molybdenum metal. A preferred range is 200 to 600 ppm. Generally, about 250–500 ppm is the most preferred level.

It has been discovered that the method of the present invention provides a process wherein the molybdenum catalyst is retained in solution in the presence of a base-treated solution of tertiary butyl hydroperoxide in tertiary butyl alcohol during the life of the reaction.

The epoxidation reaction of this invention is carried out in the presence of a polar solvent.

Tertiary butyl hydroperoxide and TBA are coproduced commercially by the oxidation of isobutane, as noted, and tertiary butyl alcohol is coproduced with the TBHP and will normally supply all of the polar solvent required for the present invention.

It is preferred that the solution of TBHP in TBA contain very little water, between zero and 1 wt.%. Preferably, the water level should be less than 0.5 wt.%.

The reaction can be carried out to achieve a hydroperoxide conversion while still maintaining high epoxide selectivities, basis the hydroperoxide reacted. This is important because the profitability of a commercial olefin epoxide plant, to a significant extent, is increased as the yield of olefin epoxide increases.

The reaction time may vary considerably, from minutes to hours. Generally, the reaction times run from thirty minutes to three or four hours with 1.5–2.0 hours being about average. The preferred single stage reaction time/ temperature is two hours at 110°–120° C. Preferably the reaction is conducted in two or more temperature stages.

The reaction procedure generally begins by charging the olefin to the reaction vessel. Next, the hydroperoxide, polar solvent and catalyst may be added and the contents heated to the desired reaction temperature. Alternatively, the olefin reactant may be heated to, at or near the preferred reaction temperature, and then the hydroperoxide, polar solvent and catalyst may be added. Further heat may be provided by the exotherm of the reaction. The reaction is then allowed to proceed for the desired amount of time at the reaction temperature, generally 110°-120° C., or conducted for 1 hour at 50°-120° C. followed by 1 hour at 120-150° C. The mixture is cooled down and the oxide recovered.

A series of reactors helps to achieve the objectives of the present invention.

A more effective approach is to use a CSTR or a series of CSTR's followed by one or more plug flow reactors because conversion can be more effectively forced to completion in a plug flow reactor.

The epoxidation reaction product, which will comprise unreacted propylene, unreacted tertiary butyl hydroperoxide, propylene oxide, tertiary butyl alcohol, and impurities, is withdrawn from the epoxidation reactor and charged to a distillation zone where it is resolved in one or a plurality of serially connected distillation columns into a plurality of distillate fractions, including a distillate propylene recycle fraction, a product propylene oxide fraction, a product tertiary butyl alcohol fraction and a residual fraction containing unrecovered tertiary butyl hydroxide, unrecovered tertiary butyl alcohol, the molybdenum epoxidation catalyst and impurities.

DESCRIPTION OF THE PREFERRED EMBODIMENT

Turning now to the drawing, there is shown a schematic flow sheet illustrating a preferred method for the continuous practice of the process of the present invention. In the drawing, conventional parts such as valves, pumps, temperature sensors, pressure sensors, heaters, coolers, control and flow regulation apparatus, reboilers, reflux condensers, etc., have been omitted.

In accordance with a preferred embodiment of the present invention, an oxidation reactor 10 is provided with an oxygen charge line 12 and an isobutane charge line 14. Within the oxidation reactor 10, oxidation reaction conditions, such as a temperature of about 90° to about 150° C. and a pressure of about 50 to about 1,000 psig. are established in order to bring about an oxidation of a portion of the isobutane fed by the charge line 14, so as to obtain a conversion of the isobutane of, for example about 20 to about 50%. As a consequence, a reaction mixture will be formed within the oxidation reaction zone 10 comprising unreacted isobutane, tertiary butyl hydroperoxide, tertiary butyl alcohol and by-products including materials such as ditertiary peroxide, acetone, methanol, and carboxylic acids such as formic acid, acetic acid and isobutyric acid, as shown in Table I above.

A stream of the oxidation reaction product is withdrawn from the oxidation reaction zone 10 by a line 16 leading to a first distillation zone comprising, for example, a distillation column 20 wherein the oxidation reaction product is separated into a lighter isobutane distillate fraction 22 that may suitably be recycled to the isobutane charge line 14 and a heavier distillation fraction discharged by a line 21 comprising a tertiary butyl alcohol solution of tertiary butyl hydroperoxide and by-products, including $C_1$ to $C_4$ carboxylic acids.

The heavy distillation fraction 21 is routed to a tertiary butyl hydroperoxide drying distillation column 23 where the tertiary butyl hydroperoxide is further concentrated and dried, being separated into a distillate tertiary butyl alcohol fraction 25 and a heavier dried solution of tertiary butyl hydroperoxide in tertiary butyl alcohol which is normally contaminated with $C_1$ to $C_4$ carboxylic acids and other oxygenated impurities.

In accordance with the present invention, and especially when the heavy distillation fraction 24 has a carboxylic acid content of more than about 1 wt.% (e.g., about 1 to about 10 wt.%), valve 28 and valve 29 will be closed and the valve 26 will be opened so that the heavier distillation fraction in the line 24 is charged to a neutralization zone, such as an autoclave 208 equiped with suitable agitation means. About ½ to about 1 equivalents of powdered calcium oxide and/or calcium hydroxide, based on the carboxylic acids contained in the heavier distillation fraction 24, is also charged to the autoclave 208 by a charge line 34. In this situation, wherein a continuous neutralization is to be accomplished, it is desirable to continuously feed the calcium oxide and/or calcium hydroxide to the autocalve 208 in order to maintain a level of about ½ to 1 equivalents of the calcium oxide or calcium hydroxide per equivalent of the carboxylic acids.

As a consequence, a slurry of the powdered calcium compound in the heavier fraction is formed, and is thoroughly mixed. Appropriate neutralization conditions are established in the autoclave 208, such as a temperature of about 70° to about 100° C., a residence time of about ½ to about 5 hours, and an appropriate pressure, such as a pressure of about 100 to about 500 psig. As a consequence, the calcium oxide and/or calcium hydroxide will partially react with the carboxylic acids present in the autoclave 208 to form a precipitate. The resultant slurry is discharged from the autoclave 208 by an autoclave discharge line 210.

By way of example, about 100 pounds per hour of the heavier distillation fraction 24 containing about 42-43 wt.% of tertiary butyl alcohol, about 55-56 wt.% of tertiary butyl hydroperoxide and about 0.7 to about 0.8 wt.% of carboxylic acids is charged by the line 24 and treated in the autoclave 208, as described with about 0.37 pound per hour of calcium hydroxide and for an average residence time of about 1 to about 5 hours at a temperature of aboaut 70° to about 100° C. and a pressure of about 100 to about 500 psig. and the resultant precipitate in the partially purified tertiary butyl alcohol solution of tertiary butyl hydroperoxide is discharged by a discharge line 210.

The slurried precipitate in the line 210 is charged to a separation zone comprising, for example, a centrifuge 220 wherein the slurry is separated into a solids fraction comprising calcium salts of precipitated carboxylic acids which is discharged by a line 222 and a filtrate fraction comprising a partially purified tertiary butyl alcohol solution of tertiary butyl hydroperoxide which is discharged by a line 224 leading to a holding tank 230, from which it can be recycled to the epoxidation reactor.

The epoxidation zone may comprise, by way of illustration, a reactor 50. The filtrate from holding tank 230 may proceed to a return tank 240 and then through line 242, through valve 28 and line 52 to be charged to the epoxidation reactor 50 together with a soluble molybdenum catalyst such as, for example, an ethylene glycol solution of an ethylene glycol/molybdenum complex formed by the reaction of ethylene glycol with ammonium heptamolybdate as shown, for example, in Marquis et al. U.S. Pat. No. 4,626,596. The catalyst solution may be added by supply line 51 to the epoxidation reactor. The calcium oxide/calcium hydroxide treated solution of tertiary butyl hydroperoxide in tertiary butyl alcohol will be charged to epoxidation reactor 50 via line 52. Only minimal precipitation of the molybdenum catalyst, if any, will be experienced because of the pretreatment of the partially purified tertiary butyl alcohol solution of tertiary butyl hydroperoxide with calcium oxide and/or calcium hydroxide in the neutralization zone 208. Propylene is added to the epoxidation reactor 50 through a propylene charge line 54, preferably in an amount such that a molar excess of olefin is charged relative to the charge of tertiary butyl hydroperoxide, e.g., propylene may be charged at a rate of from about 1.5 to about 5 moles of propylene per mol of tertiary butyl hydroperoxide charged.

Within the reactor 50 at least a portion of the propylene and at least a portion of the tertiary butyl hydroperoxide catalytically react to form additional tertiary butyl alcohol and propylene oxide and to provide a reaction product comprising unreacted propylene, propylene oxide, tertiary butyl alcohol, tertiary butyl hydroperoxide, and oxygen-containing impurities including $C_1$ to $C_4$ carboxylic acids such as formic acid, acetic acid, isobutyric acid, etc.

A stream of the reaction product is withdrawn from the reactor 50 by way of a discharge line 56 leading to the primary fractionator 60. It will be understood that the distillation zone may comprise a single column in which the several fractions are recovered as an overhead fraction or sidestream fractions, or as a plurality of splitter columns as shown schematically in the drawing. The discharge stream 56 is charged to the primary fractionation column 60 where a distillate fraction comprising propylene and propylene oxide is taken overhead by a line 61. The overhead fraction 61 is fed to the propylene recycle distillation zone 70. A propylene distillate fraction 62 is recycled from the propylene recycle distillation zone 70 to the line 54 leading to the epoxidation reactor 50. A heavier crude propylene oxide distillation fraction 72 is discharged from the propylene recycle distillation zone 70 for further treatment in a propylene oxide purification zone (not shown).

The bottoms fraction 74 from the primary fractionator 60 is charged to a distillation column 80 wherein an overhead distillate composed primarily of tertiary butyl alcohol leaves via line 82. The tertiary butyl alcohol distillate fraction 82 remains contaminated with contaminants including $C_1$ to $C_4$ carboxylic acids and other oxygenated impurities. The bottoms fraction 84 from distillation column 80 is charged to an evaporation zone 200.

The distillate tertiary butyl alcohol fraction in line 82 may be recovered as a product. However, it is sometimes desirabe to recycle the fraction in line 82 to the epoxidation reactor 50 in order to maintain a properly diluted solution of tertiary butyl hydroperoxide therein. However, although the distillation column 80 is preferably operated to provide a cut point such the acidic impurities charged to the distillation column 80, including carboxylic acids containing 1 to 4 carbon atoms, will be concentrated in the bottoms fraction 84, there is a tendency due to azeotrope formation, distillation column upsets, etc. for the acidic impurities to azeotrope with the tertiary butyl alcohol or to otherwise become entrained therewith so that the distillate tertiary butyl alcohol fraction 82 will be contaminated with about 1 wt.% to 5 wt.% of carboxylic acids and to thus be unsuitable for recycle to the epoxidation reaction zone 50.

In this situation, the valve 83 may be partially or wholly closed and all or a part of the contaminated distillate tertiary butyl alcohol fraction 82 may be routed by a branch line 85 controlled by a valve 29 to a neutralization zone 208 which may comprise an autoclave equipped with suitable agitation means and to which about ½ to about 1 equivalents of powdered calcium oxide and/or calcium hydroxide, based on the carboxylic acids contained in the contaminated distillate tertiary butyl alcohol fraction 82 is charged by way of a charge lines 85 and 34. Again, since a continuous neutralization is to be accomplished, the calcium oxide and/or calcium hydroxide is continuously fed to the autoclave 208 in order to maintain a level of ½ to 1 equivalents of the calcium oxide or calcium hydroxide per equivalent of the carboxylic acids.

Appropriate neutralization conditions are established in the autoclave 208, as described above, such as a temperature of about 70° to about 100° C., a residence time of about ¼ to about 5 hours, and an appropriate pressure, such as atmospheric pressure. As a consequence, the calcium oxide and/or calcium hydroxide will partially react with the carboxylic acids present in the autoclave 208 to form a precipitate. The resultant slurry is discharged from the autoclave 208 by an autoclave discharge line 210.

The slurried precipitate in the line 210 is charged to a separation zone comprising, for example, a centrifuge 220 wherein the slurry is separated into a solids fraction comprising calcium salts of precipitated carboxylic acids which is discharged by a line 222 and a second filtrate fraction comprising partially purified tertiary butyl alcohol which is discharged by a line 224.

As indicated, the distillation column 80 is preferably operated so that a maximized amount of the acidic impurities discharged from the epoxidation reaction zone 50, including carboxylic acids containing 1 to 4 carbon atoms, will be concentrated in the bottoms fraction discharged by line 84.

The bottoms fraction 84 will normally contain tertiary butyl alcohol, unreacted tertiary butyl hydroperoxide, oxygenated impurities including $C_1$ to $C_4$ carboxylic acids, the molybdenum catalyst, etc., and is charged to an evaporation zone 200 where a solution of tertiary butyl hydroperoxide in tertiary butyl alcohol is taken overhead by a line 204 leading to a charge line 205 for neutralization zone 208. The bottoms fraction 202 from the evaporator 200 is a residue fraction that will typically have the composition shown in Table II.

TABLE II

| COMPOSITION OF RESIDUE FRACTION | |
|---|---|
| Component | Concentration, Wt. % |
| t-butyl hydroperoxide | 40–45 |
| t-butyl alcohol | 45–40 |
| Residue, including $C_1$–$C_4$ carboxylic acids | 10–15 |
| Molybdenum, ppm | 500–5,000 |

From the table, it will be seen that the bottoms fraction 84 is highly contaminated and not ameanable to separation into pure tertiary butyl alcohol and tertiary butyl hydroperoxide fractions by conventional distillation techniques.

However, in accordance with the present invention, a usable stream comprising a mixture of tertiary butyl alcohol and tertiary butyl hydroperoxide can be obtained by routing the bottoms fraction 84 to an evaporation zone 200, comprising, for example, a wiped film evaporator wherein the bottoms fraction 84 is resolved into a residue fraction that is discharged from the wiped film evaporator 200 by a discharge line 202 and a condensate fraction discharged from the wiped film evaporator by a line 204. The condensate fraction 204 will normally be contaminated with significant quantities of acidic materials including, for example, from about 1 to about 10 wt.% of carboxylic acids containing 1 to 4 carbon atoms.

In accordance with the present invention, the condensate fraction 204 may be routed via line 205 to a neutralization zone 208 constructed and operated as described above. The condensate fraction 204 is continuously charged to the autoclave 208 via line 205 together with about ¼ to about 1 equivalents of powdered calcium oxide and/or calcium hydroxide, based on the carboxylic acids contained in the contaminated condensate fraction 204, the calcium oxide and/or calcium hydroxide being continuously charged to the autoclave 208. Appropriate neutralization conditions are established in the autoclave 208, as described above, such as a temperature of about 70° to about 100° C., a residence time of about ¼ to about 5 hours, and an appropriate pressure, such as atmospheric pressure. As a consequence, the calcium oxide and/or calcium hydroxide will partially react with the carboxylic acids present in the autoclave 208 to form a precipitate. The resultant slurry is discharged from the autoclave 208 by an autoclave discharge line 210 leading to the centrifuge 220 wherein the slurry is separated into a solids fraction comprising calcium salts of precipitated carboxylic acids which is discharged by a line 222 and a filtrate fraction comprising a partially purified stream of tertiary butyl alcohol and tertiary butyl hydroperoxide which is discharged by a line 224 to a holding tank 230. This treated material may be routed through return tank 240 to the epoxidation reactor 50 via line 242.

EXAMPLES

The invention will be further illustrated by the following specific examples which are laboratory experiments that were conducted in a manner to verify the discoveries that have been made. Accordingly, precisely controlled amounts of base were used. The neutralization reactions were conducted in glass bottles at atmospheric pressure (and therefore had to be conducted at room temperature) for prolonged periods of time to make sure that the reactions went substantially to completion. It will be understood, as illustrated above, that in conducting a continuous process larger quantities of the calcium oxide and/or calcium hydroxide could be used and the reactions would be conducted over significantly shorter reaction periods at elevated temperatures.

Example 1 (6333-11)

To a pint bottle was added 300.0g of peroxidate* solution (obtained by isobutane oxidation and containing 55.48% of tertiary butyl hydroperoxide (TBHP), having an acid number of 11.08 mg KOH/g, and a formic acid content of 0.56 wt.% formate, and an acetic acid content of 0.18 wt.% acetate, and 0.07% isobutyrate) followed by 3.14g of anhydrous $Na_2CO_3$ (MW 106, 0.0296 mols, 0.0592 equivalents of base). This slurry was stirred for four days at room temperature and filtered. The filtrate contained 54.74% TBHP, had an acid number of 0.65 mg KOH/g and had a formate content of 0.02 wt.%, acetate =0.13 wt.% and isobutyrate=0.10 wt.%. The filtered base treated peroxidate (164.41g) was stirred with 0.442g of a fresh catalyst comprising an ethylene glycol solution of a molybdenum/ethylene glycol complex containing 13.0% moly (moly-EG catalyst 5990-32-2). Based on a total weight of 164.852g (164.41+0.442g) the expected molybdenum (moly) level was 349 ppm. After stirring for two days at room temperature, the hazy solution was filtered and the filtrate analyzed for ppm moly and found to contain only 79.0 ppm moly or 22.6% of that charged. The peroxidate treated with $Na_2CO_3$ caused precipitation of the majority of the soluble molybdenum catalyst charged.

*300.0 Grams of peroxidate contained 0.059251 mole acid basis the observed acid number of 11.08.

Example 2 (6333-12)

To a pint bottle was added 300.0g of peroxidate (same as in Example 1) and 1.66g of anhydrous KOH (MW 56.1, 0.0296 mols). This clear solution was stirred for four days at room temperature and was analyzed and found to contain 53.57% TBHP, acid number of 4.86, and formate content was 0.44 wt.%, acetate was 0.20 wt.% and isobutyrate was 0.06 wt.%. The base treated peroxidate (168.00 grams) was stirred with 0.449g of moly-EG catalyst 5990-39-2 (13.0moly). Based on total weight of 168.559g the expected moly level was 346 ppm. After stirring two days at room temperature the hazy solution was filtered and analyzed and the filtrate found to contain only 16 ppm moly or 4.6% of that charged. The base treated peroxidate caused precipitation of nearly all of the molybdenum charged.

Example 3 (6333-13)

To a pint bottle was added 300.0g of peroxidate (same as in Example 1) and 1.19g of anhydrous NaOH (MW 40, 0.0298 mols). The hazy solution was stirred for four days at room temperature and was filtered. The filtrate was analyzed and found to contain 53.34% TBHP, acid number of 4.82, and formate content of 0.12 wt.%, acetate was 0.21 wt.% and isobutyrate was 0.12 wt.%. The base treated filtrate (168 73g) was stirred with 0.450g of moly-EG catalyst 5990-39-2 (13.0% moly). Based upon total weight of 169.18g the expected moly level was 346 ppm. After stirring 2 days at room temperature, the hazy solution was filtered and the filtrate analyzed and found to contain 210 ppm moly or 60.7% of that charged. The base-treated peroxidate caused precipitation of nearly 40% of the molybdenum charged.

Example 4 (6333-14)

To the peroxidate described in Example 1 (300.0 grams) was added 3.30g of anhydrous potassium t-butoxide and 46.7g of t-butyl alcohol (MW of KOt-Bu=112.1, 0.0294 mols added). The clear solutin was stirred for four days at room temperature and was found to contain 46.57% TBHP (97.1% of that charged, 46.5% of 350.0g), acid number of 3.94, formate=0.39 wt.%, acetate=0.17 wt.%, and isobutyrate=0.13 wt.%. The base treated filtrate (193.26g) was stirred with 0.497g of moly-EG catalyst 5990-39-2 (13.0% moly). Based upon a total weight of 193.57g the expected moly level was 333 ppm. After stirring for 2 days at room temperature the hazy solution was filtered and the filtrate analyzed for moly and found to contain <10 ppm or less than 3.0% of the moly charged. The base treated peroxidate caused precipitation of more than 97% of the molybdenum charged.

Example 5 (6333-15)

To the peroxidate described in Example 1 (300.0g) was added 2.85g of anhydrous sodium t-butoxide and 197.15g of t-butyl alcohol (MW of NaOtBu 32 97, 0.0297 mols). The hazy solution was stirred for four days at room temperature and was filtered. The filtrate was analyzed and found to contain 32.69% TBHP (97.8% of that charged, 32.69% ×500.0g), acid number of 3.56, formate=0.07 wt.%, acetate=0.13 wt.%, and isobutyrate =0.08 wt.%. The base treated filtrate 275.31g was stirred with 0.654g of moly-EG catalyst 5990-39-2 (13.0% moly). Based on a total weight of 275.964g the expected moly level was 308 ppm. After stirring for two days at room temperature, the hazy solution was filtered and the filtrate analyzed for molybdenum and found to contain 160 ppm or 51.9% of the moly charged. The base-treated peroxidate caused precipitation of nearly half of the moly charged.

Example 6 (6333-34)

To the peroxidate described in Example 1 (300.0g) was added 1.75g of concentrated ammonium hydroxide solution (28.8% NH$_3$, 0.504g NH$_3$, 0.0296 mols NH$_3$). The clear solution was stirred for 12 days at room temperature and was analyzed and found to contain 53.77% TBHP and an acid number of 8.77 mg KOH/g sample. To the clear base-treated peroxidate (168.00g) was added 0.44g of moly-EG catalyst (5990-39-2, moly=13.0%). The cloudy mixture, with some precipitate visible, was stirred for two days at room temperature and was filtered. The filtrate was analyzed and found to contain only 14 ppm molybdenum or only 4.1% of that charged (expected moly in solution was 340 ppm). The base-treated peroxidate again caused precipitation of nearly all of the molybdenum charged. The filtrate was also analyzed for TBHP=54.55%, acid number=7.77 mg KOH/g, formate=0.31 wt.%, acetate=0.20 wt.%, and isobutyrate=0.14 wt.%.

Example 7 (6333-35)

To the peroxidate described in Example 1 (300.0g) was added 1.10g of Ca(OH)$_2$ (0.0148 mols, 0.0296 equivalents). The slurry was stirred for 12 days at room temperature and filtered. The filtrate was found to contain 53.95% TBHP, and an acid number of 5.10 mg KOH/g sample. To the base treated filtrate (164.0g) was added 0.44g of moly-EG cata lyst 5990-39-2 (13.0% moly). Based on a total weight of 164.44g the expected moly level was 348 ppm. The slightly hazy solution was stirred for two days at room temperature and filtered. The filtrate was analyzed and was found to contain 349 ppm moly (100.3% of the moly charged), 53.99% TBHP, acid number of 4.95 mg KOH/g and a formate content of 0.07 wt.%, acetate =0.20 wt.% and isobutyrate=0.13 wt.%. Here, the base-treated peroxidate had the acidity reduced (by about 50%) but did not precipitate the moly catalyst as was observed in all other previous examples.

Example 8 (6333-36)

To the peroxidate described in Example 1 (300.0g) was added 0.83g CaO (0.0148 mols, 0.0296 equivalents). The slurry was stirred for 12 days at room temperature and filtered. The filtrate was found to contain 53.81% TBHP, and an acid number of 7.64 mg KOH/g. To the base treated filtrate (166.0g) was added 0.44g of moly EG catalyst 5990-39-2 (13.0% moly). Based on a total weight of 166.44g the expected moly level was 344 ppm. The slightly hazy solution was stirred for two days at room temperature and was filtered. The filtrate was analyzed and was found to contain 349 ppm moly (101.4% of the moly charged), 53.61% TBMP, an acid number of 8.85 mg KOH/g sample, and a formate content of 0.23 wt.%, acetate =0.20 wt.%, and isobutyrate=0.13 wt.%. Here, again the base-treated peroxidate did not precipitate molybdenum as did the previous bases examined in Examples 1-6. The CaO described in this example did not remove acidity as efficiently as Ca(OH)$_2$ described above in Example 7, but like the Ca(OH)$_2$ did not cause molybdenum precipitation.

A summary of the data (results) from Examples 1-8 is presented in Tables III-A and III-B, attached.

TABLE III-A

TREATMENT OF PILOT PLANT PEROXIDATE DISTILLATION BOTTOMS WITH VARIOUS BASES TO DETERMINE WHICH BASES REDUCE ACIDITY AND WHICH ACIDS, IF ANY, ARE REMOVED BY BASE TREAMENT. ALSO, ADDITION OF MOLYBDENUM TO THE BASE-TREATED PEROXIDATES TO SEE IF MOLYBDENUM IS SOLUBLE.

| 1 NB Run # | 2 NB # of the Feed Charged | 3 Reaction Conditions Time | 4 Grams TBHP Charged | 5 G Moles Acid Charged | 6 Equiv Base/ Equiv Acid | 7 Grams Formate Charged to the Peroxide | 8 Grams Acetate Charged to the Peroxide | 9 Grams Isobutyrate Chgd to the Peroxide | 10 Base Charged (Grams) | 11 Base Charged Equiv |
|---|---|---|---|---|---|---|---|---|---|---|
| 6333-11 | 6333-4-1 | RT 96 hrs | 166.44 | .059251 | 1/1 | 1.6800 | 0.5400 | 0.2100 | NA$_2$CO$_3$ (3.14) | NA$_2$CO$_3$ 0.0592 |
| 6333-13 | 6333-4-1 | RT 96 hrs | 166.44 | .059251 | 0.5/1 | 1.6800 | 0.5400 | 0.2100 | NAOH (1.19) | NAOH 0.0298 |
| 6333-15 | 6333-4-1 | RT 96 hrs | 166.44 | .059251 | 0.5/1 | 1.6800 | 0.5400 | 0.2100 | NAOTBU (2.85) | NAOTBU 0.0297 |
| 6333-12 | 6333-4-1 | RT 96 hrs | 166.44 | .059251 | 0.5/1 | 1.6800 | 0.5400 | 0.2100 | KOH (1.66) | KOH 0.0296 |
| 6333-14 | 6333-4-1 | RT 96 hrs | 166.44 | .059251 | 0.5/1 | 1.6800 | 0.5400 | 0.2100 | KOTBU (3.30) | KOTBU 0.0294 |
| 6333-34 | 6333-4-1 | RT 288 hrs | 166.44 | .059251 | 0.5/1 | 1.6800 | 0.5400 | 0.2100 | NH$_4$OH (0.504)* | NH$_4$OH 0.0296 |
| 6333-35 | 6333-4-1 | RT 288 hrs | 166.44 | .059251 | 0.5/1 | 1.6800 | 0.5400 | 0.2100 | CA(OH)$_2$ (1.10) | CA(OH)$_2$ 0.0296 |
| 6333-36 | 6333-4-1 | RT 288 hrs | 166.44 | .059251 | 0.5/1 | 1.6800 | 0.5400 | 0.2100 | CAO | CAO |

TABLE III-A-continued

TREATMENT OF PILOT PLANT PEROXIDATE DISTILLATION BOTTOMS WITH VARIOUS BASES TO DETERMINE WHICH BASES REDUCE ACIDITY AND WHICH ACIDS, IF ANY, ARE REMOVED BY BASE TREAMENT. ALSO, ADDITION OF MOLYBDENUM TO THE BASE-TREATED PEROXIDATES TO SEE IF MOLYBDENUM IS SOLUBLE.

| 1 NB Run # | 2 NB # of the Feed Charged | 3 Reaction Conditions Time | 4 Grams TBHP Charged | 5 G Moles Acid Charged | 6 Equiv Base/ Equiv Acid | 7 Grams Formate Charged to the Peroxide | 8 Grams Acetate Charged to the Peroxide | 9 Grams Isobutyrate Chgd to the Peroxide | 10 Base Charged (Grams) | 11 Base Charged Equiv |
|---|---|---|---|---|---|---|---|---|---|---|
| | | | | | | | | | (0.83) | 0.0296 |

Amount of feed 300 grams for all runs
6333-4-1 = Pilot plant peroxide distillation bottoms, TBHP = 55.48 wt. %
RT = Room temperature
* = Grams NH₃
In the base-treated peroxidates where solids formed upon base treatment, the solids were filtered before moly was added.

TABLE III-B

TREATMENT OF PILOT PLANT PEROXIDATE DISTILLATION BOTTOMS WITH VARIOUS BASES TO DETERMINE WHICH BASES REDUCE ACIDITY AND WHICH ACIDS, IF ANY, ARE REMOVED BY BASE TREATMENT. ALSO, ADDITION OF MOLYBDENUM TO THE BASE-TREATED PEROXIDATES TO SEE IF MOLYBDENUM IS SOLUBLE.

| NB Run # | 12 Grams Solvent used to Dissolve Base | 13 Physical State After Treatment | 14 G TBHP in Liquid After Treatment | 15 TBHP in Liquid After Treatment (% of Feed) | 16 G Moles of Acid in Liquid After Treatment | 17 Acid in Liquid After Treatment (% of Feed) | 18 ppm Moly Added to Base-Treated Peroxide | 19 After Stirring & Filtration ppm Moly Remaining in Solution | 20 % of MO Fed that Remains in the Base-Treated Peroxide |
|---|---|---|---|---|---|---|---|---|---|
| 6333-11 | None | Solids/Filtered | 164.22 | 98.7 | .003476 | 5.9 | 349.0 | 79.0 | 22.6 |
| 6333-13 | None | Solids/Filtered | 160.02 | 96.1 | .027487 | 46.4 | 346.0 | 210.0 | 60.7 |
| 6333-15 | 197.15 (TBA) | Solids/Filtered | 162.52 | 97.6 | .031548 | 53.2 | 308.0 | 160.0 | 51.9 |
| 6333-12 | None | Clear | 161.60 | 97.1 | .026133 | 44.1 | 346.0 | 16.0 | 4.6 |
| 6333-14 | 46.70 (TBA) | Clear | 163.00 | 97.9 | .024581 | 41.5 | 333.3 | <10.0 | <3.0 |
| 6333-34 | None | Clear | 162.25 | 97.5 | .047172 | 79.6 | 340.0 | 14.0 | 4.1 |
| 6333-35 | None | Solids/Filtered | 162.44 | 97.6 | .027373 | 46.2 | 348.0 | 349.0 | 100.3 |
| 6333-36 | None | Solids/Filtered | 161.88 | 97.3 | .040969 | 69.1 | 344.0 | 349.0 | 101.4 |

In the base-treated peroxidates where solids formed upon base treatment, the solids were filtered before moly was added.

Turning now to Table III, the most complete removal of acid contaminants was obtained with sodium carbonate, in Run No. 6333-11, in that the sodium carbonate precipitated about 95% of the total acids present in the feedstock. In this run an equivalent amount of base was fed relative to the amount of acid present. In runs 6333-13, 6333-15, 6333-12, 6333-14, 6333-34, 6333-34, 6333-35 and 6333-36 only 0.5 equivalent of base was used per equivalent of acid in the feed to be treated. Therefore, the expected amount of acids remaining in the liquid should be 50% of that fed. In fact the average amount of acid left in the liquid in the last seven runs, (Table III-B column 17) is 54.32%. Thus, significantly larger percentages of the acid contaminants remained in the liquid after treatment with the other basic reagents used, ranging from about 41.5% to about 79.6%, and constituting only about 69% for Run No. 6333-36 wherein calcium oxide was used, and about 46% for Run No. 6333-35 wherein calcium hydroxide was used.

Thus, as expected, the base treatment with about ½ equivalent of base resulted in a partial purification of the feedstock in all instances.

However, note that when the molybdenum catalyst was added to the filtrate, about 73% of the molybdenum prepcipitated from the filtrate resulting from treatment with sodium carbonate (Run No. 6333-11, Table III-B, column 20). About half of the molybdenum precipitated from the filtrate when sodium hydroxide and sodium butoxide were used (Run No. 6333-13 and Run No. 6333-15, respectively). In excess of 90% of the molybdenum precipitated when potassium hydroxide, potassium butoxide and ammonium hydroxide were used (Run No. 6333-12, Run No. 6333-14, and Run No. 6333-34, respectively).

In contrast, when calcium oxide and calcium hydroxide were used, it was found, within the range of experimental error, that substantially all of the molybdenum remained in the filtrate (Run No. 6333-35 and Run No. 6333-36). In other words, treatment of an acidic tertiary butyl alcohol solution of tertiary butyl hydroperoxide with ½ of an equivalent of calcium oxide or calcium hydroxide, basis the acidity of the tertiary butyl alcohol solution of tertiary butyl hydroperoxide, followed by filtration of the solids, afforded a filtrate which did not precipitate the molybdenum catalyst to be used in the epoxidation reaction. In both of runs 6333-35 and 6333-36, the analysis indicated that slightly more than 100% of the charged molybdenum remained in solution in the filtrate. These numerical values are numbers obtained within the range of experimental accuracy.

Preparation of Olefin Epoxide using the Present Invention

Example 9

Preparation of Moly Catalyst 5990-39-2 Moly EG Catalyst

To a 500-ml round bottomed flask equipped with a magnetic stirrer, thermometer, K-head, and condenser was added 196.2g of ethylene glycol (3.164 moles) and 53.80g of ammonium dimolybdate (0.3165g atoms moly). The mole ratio of ethylene glycol to gram atoms of moly was 10/1. The reaction mixture was padded with nitrogen and heated to 100° C. with stirring and held at 100° C. for 1.0 hour. The reaction mixture was cooled to 85° C. and a vacuum of 45 mm was pulled. The reaction mixture (under vacuum of 45 mm) was heated to 100° C. and held at 100° C. (30 mm vacuum) for 10 minutes and then cooled. The reaction mixture was light yellow in color and solids free. The overhead weighed 12.0 grams (47.45% water) and the cold trap weighed 1.6 grams (89.44% water). The stripped product catalyst weighed 231.6 grams (92.64% of the total charge). The product was analyzed and found to contain 13.0% molybdenum (atomic absorption spectroscopy), 1.00% nitrogen, 0.74% water and have an acid number of 152.69 mgKOH/g sample.

Example 10

Epoxidation of Octene-1 with Base Treated Peroxidate (6333-47)

100.0g Peroxidate (6333-4-1) was found to contain 0 019750 moles acid (acid #=11.08 mgKOH/g) so it was treated with 0.585g Ca(OH)$_2$ (MW=74.1, equiv. wt.=37.05, 0.0158 equivalents of base or 80% of the acid present). The peroxidate and Ca(OH)$_2$ were allowed to stir for several days at room temperature. The base-treated peroxidate was filtered and analyzed and found to contain 55.15% TBHP (balance TBA), and had an acid #of 4.17 mgKOH/g sample. To 34.3g of the base-treated and filtered TBHP (TBHP=55.15%, and acid #=4.17 mgKOH/g sample) was added 0.154g of moly-EG catalyst (5990-39-2, 13.0% moly) in a 250 ml round-bottomed flask equipped with a mechanical stirrer, thermometer, N$_2$ pad, and conserver. To the TBHP-moly EG catalyst solution was added 45.7g of 1-octene (Aldrich). The reaction mixture was heated to 95° C. and held there 2.0 hours. Product weighed 80.1 grams.

Analysis of the reaction mixture found % TBHP =3.54% and ppm moly=271.

$$\text{Conversion TBHP} = \frac{\text{moles TBHP reacted}}{\text{moles TBHP fed}} = \frac{\text{moles fed-moles remaining}}{\text{moles fed}} = 85.0\%$$

$$\text{Selectivity to octene oxide (basis TBHP reacted)} = \frac{\text{moles octene oxide}}{\text{moles TBHP reacted}} = 88.2\%$$

$$\text{Moly balance} = \frac{\text{g moly out}}{\text{g moly fed}} = \frac{.02172}{.02002} = 108.5\%$$

The foregoing examples are given by way of illustration only and are not intended as limitations on the scope of this invention as defined by the claims appended hereto.

We claim:

1. In a method wherein isobutane is reacted with oxygen to provide a reaction product comprising unreacted isobutane, tertiary butyl hydroperoxide, tertiary butyl alcohol and carboxylic acid impurities, including formic acid, acetic acid and isobutyric acid, the improvement which comprises the steps of:
   a. charging said reaction product to a first distillation zone and separating it therein into at least a lighter isobutane recycle fraction and a heavier distillation fraction comprising tertiary butyl hydroperoxide, tertiary butyl alcohol and carboxylic acid impurities, including formic acid, acetic acid and isobutyric acid,
   b. charging said heavier distillation fraction to a neutralization zone and treating said heavier distillation fraction therein with about ½ to about 1 equivalent of calcium hydroxide and/or calcium oxide, based on the carboxylic acid content of said heavier distillation fraction to thereby provide a slurry of solid precipitate in said thus-treated heavier distillation fraction,
   c. charging said slurry to a separation zone and separating it therein into a solids fraction and a liquid filtrate fraction comprising said partially purified heavier distillation fraction comprising tertiary butyl hydroperoxide, tertiary butyl alcohol, and about 5 to about 50 wt.% of the said carboxylic acid impurities initially present in said heavier distillation fraction, and
   d. recovering said filtrate,
   e. charging said filtrate to an epoxidation reaction zone together with a soluble molybdenum epoxidation catalyst and a molar excess of an olefin containing about 3 to 10 carbon atoms, based on the tertiary butyl hydroperoxide in said filtrate and reacting the tertiary butyl hydroperoxide in said filtrate with said olefin in said epoxidation reaction zone under epoxidation reaction conditions without substantial precipitation of molybdenum to provide an epoxidation reaction product comprising unreacted olefin, an olefin epoxide corresponding to said olefin, additional tertiary butyl alcohol, and impurities, and
   f. charging said epoxidation reaction product from said epoxidation reaction zone to a second distillation zone and separating it therein into a plurality of distillation fractions including an unreacted olefin fraction, an olefin epoxide product fraction, a tertiary butyl alcohol product fraction and a residue fraction.

2. A method as in claim 1 wherein the oxidation reaction product contains about 50 to about 80% of unreacted isobutane, and wherein the heavier distillation fraction comprises a solution of at least about 30 wt.% of tertiary butyl hydroperoxide in tertiary butyl alcohol.

3. A method as in claim 1 wherein said oxidation reaction product contains from about 50 to about 80 wt.% of isobutane, from about 25 to 55 wt.% of tertiary butyl hydroperoxide, from about 25 to about 55 wt.% of tertiary butyl alcohol and about 0.05 to about 2 wt.% of said carboxylic acid impurities.

4. A method as in claim 3 wherein said heavier distillation fraction is treated with about ½ equivalent of calcium hydroxide and/or calcium oxide, based on the carboxylic acid content of said heavier distillation fraction and wherein the said filtrate fraction contains about 50 wt.% of the said carboxylic acid impurities initially present in said heavier distillation fraction.

5. A method as in claim 4 wherein said heavier distillation fraction is treated with about ½ equivalent of calcium oxide.

6. A method as in claim 4 wherein said heavier distillation fraction is treated with about ½ equivalent of calcium hydroxide.

7. A continuous method which comprises the steps of:
   continuously reacting isobutane with oxygen to provide an oxidation reaction product comprising unreacted isobutane, tertiary butyl hydroperoxide, tertiary butyl alcohol and carboxylic acid impurities, including formic acid, acetic acid and isobutyric acid,
   a. continuously charging a stream of said oxidation reaction product to a first distillation zone and separating said oxidation reaction product therein into at least a lighter isobutane recycle fraction and a heavier distillation fraction comprising tertiary butyl hydroperoxide, tertiary butyl alcohol and at least 1 wt.% of carboxylic acid impurities, including formic acid, acetic acid and isobutyric acid,
   b. continuously charging said heavier distillation fraction to a neutralization zone and continuously treating said heavier distillation fraction therein with about ½ to about 1 equivalent of calcium hydroxide and/or calcium oxide, based on the carboxylic acid content of said heavier distillation fraction under treating conditions including a temperature of about 70° C. to about 100° C., a pressure of about 100 to about 500 psig and an average residence time of about 0.5 to 5 hours, to thereby provide a slurry of solid precipitate in said thus-treated heavier distillation fraction,
   c. continuously charging said slurry to a separation zone and continuously separating it therein into a solids fraction and a liquid filtrate fraction comprising said partially purified heavier distillation fraction which contains tertiary butyl hydroperoxide, tertiary butyl alcohol, and about 5 to about 50 wt.% of the said carboxylic acid impurities initially present in said heavier distillation fraction, and
   d. continuously recovering said filtrate,
   e. continuously charging said filtrate to an epoxidation reaction zone together with a soluble molybdenum epoxidation catalyst and a molar excess of propylene, based on the tertiary butyl hydroperoxide in said filtrate and reacting the tertiary butyl hydroperoxide in said filtrate with said propylene in said epoxidation reaction zone under epoxidation reaction conditions with significant precipitation of molybdenum to provide an epoxidation reaction product comprising unreacted propylene, propylene oxide, additional tertiary butyl alcohol, and impurities, and
   f. charging said epoxidation reaction product from said epoxidation reaction zone to a second distillation fractions including an unreacted olefin fraction, an olefin epoxide product fraction, a tertiary butyl alcohol product fraction and a residue fraction.

8. A method as in claim 7 wherein the oxidation reaction product contains about 50 to about 80% of unreacted isobutane, wherein the heavier distillation fraction comprises a solution of at least about 30 wt.% of tertiary butyl hydroperoxide in tertiary butyl alcohol.

9. A method as in claim 8 wherein said oxidation reaction product contains from about 50 to about 80 wt.% of isobutane, from about 25 to 55 wt.% of tertiary butyl hydroperoxide, from about 25 to about 55 wt.% of tertiary butyl alcohol and about 0.05 to about 2 wt.% of said carboxylic acid impurities.

10. A method as in claim 9 wherein said heavier distillation fraction is treated with about ½ equivalent of calcium hydroxide and/or calcium oxide, based on the carboxylic acid content of said heavier distillation fraction and wherein the said filtrate fraction contains about 50 wt.% of the said carboxylic acid impurities initially present in said heavier distillation fraction.

11. A method as in claim 10 wherein said heavier distillation fraction is treated with about ½ equivalent of calcium oxide.

12. A method as in claim 10 wherein said heavier distillation fraction is treated with about ½ equivalent of calcium hydroxide.

13. A method as in claim 7 wherein said distillate tertiary butyl alcohol fraction is continuously charged to a second neutralization zone and continuously treated therein under treating conditions including a temperature of about 70° to about 100° C. and an average residence time of about 1 to 5 hours with about ½ to 1 equivalents of calcium hydroxide and/or calcium oxide, based on the carboxylic acid content of said distillate tertiary butyl hydroxide fraction to thereby provide a second slurry of solid precipitate in said thus-treated distillate tertiary butyl hydroxide fraction,
   wherein said second slurry is continuously charged to a separation zone and continuously separating it therein into a solids fraction and a second liquid filtrate fraction comprising a further purified distillate tertiary butyl alcohol fraction, and
   wherein said second filtrate is continuously recovered.

14. A method as in claim 7 wherein:
   a. said residue fraction is charged to a third distillation zone and separated therein into a lighter distillate fraction comprising tertiary butyl alcohol, tertiary butyl hydroperoxide and about 1 to about 10 wt.% of carboxylic acid impurities and a heavier distillation residue fraction comprising impurities and substantially all of the molybdenum initially present in said epoxidation reaction product charged to said third distillation zone,
   b. continuously charging said lighter distillate fraction to a third neutralization zone and continuously treating said lighter distillate fraction therein under treating conditions including a temperature of about 70° to about 100° C., a pressure of about 100 to about 500 psig. and an average residence time of about 1 to 5 hours with about ½ to 1 equivalents of calcium hydroxide and/or calcium oxide, based on the carboxylic acid content of said lighter distillate fraction to thereby provide a third slurry of solid precipitate in said thus-treated distillate lighter distillate fraction,
   c. wherein said third slurry is continuously charged to a third separation zone and continuously separated therein into a solids fraction and a third liquid filtrate fraction comprising a further purified lighter distillate fraction, and
   d. wherein said third filtrate is continuously recovered.

* * * * *